United States Patent [19]

Vora et al.

[11] Patent Number: 5,008,467

[45] Date of Patent: Apr. 16, 1991

[54] PROCESS FOR DIRECT ETHERIFICATION OF A DEHYDROGENATED EFFLUENT

[75] Inventors: Bipin V. Vora, Darien; Norman H. Scott, Arlington Heights, both of Ill.

[73] Assignee: UOP, Des Plaines, Ill.

[21] Appl. No.: 445,503

[22] Filed: Dec. 4, 1989

[51] Int. Cl.$^5$ .............................................. C07L 41/06
[52] U.S. Cl. .................................... 568/697; 585/315; 585/324
[58] Field of Search .......................................... 568/697

[56] References Cited

U.S. PATENT DOCUMENTS

| | | | |
|---|---|---|---|
| 2,720,547 | 10/1955 | Wolff et al. | 260/614 |
| 4,118,425 | 10/1978 | Herbtsman | 260/614 A |
| 4,219,678 | 8/1980 | Obenaus et al. | 568/697 |
| 4,307,254 | 12/1981 | Smith, Jr. | 568/697 |
| 4,329,516 | 5/1982 | Al-Muddarris | 568/697 |
| 4,465,870 | 8/1984 | Herskovits | 568/697 |
| 4,504,687 | 3/1985 | Jones, Jr. | 568/697 |

OTHER PUBLICATIONS

Chemical Engineering News, Jun. 25, 1979 edition, p. 35 Huls-Process; Methyl Tertiary Butylether, presented at the American Institute of Chemical Engineers, 85th National Meeting on 6-4-78, by F. Obenaus et al.
Oil and Gas Journal, Dec. 8, 1980 edition, beginning at p. 96.

Article in Oil and Gas Journal, Nov. 10, 1980 edition beginning at p. 191.
Hydrocarbon Processing, Oct., 1980 edition, p. 91.

*Primary Examiner*—Howard T. Mars
*Attorney, Agent, or Firm*—Thomas K. McBride; John G. Tolomei

[57] ABSTRACT

An integrated process of producing MTBE by the dehydrogenation of isobutane and the etherification of the resulting isobutene with methanol is simplified by directly charging the effluent of a dehydrogenation zone without prior separation to an etherification zone arranged to provide countercurrent contact of isobutene and the methanol reactants such that an MTBE product is recovered as a bottoms stream and a relatively isobutene-free overhead stream is recycled to the dehydrogenation zone. Overall separation facilities are simplified by only separating $C_3$ hydrocarbons from the etherification zone product stream. This arrangement eliminates $C_3$ separation facilities ahead of the etherification zone and reduces the quantity of $C_4$ hydrocarbons that are received by the separation zone. The reaction zone may contain a series of beds arranged to further eliminate the carry over of isobutene to the separation facilities. This arrangement also allows a recovery of unreactive or unreacted $C_4$ hydrocarbons from the top of the etherification zone.

18 Claims, 2 Drawing Sheets

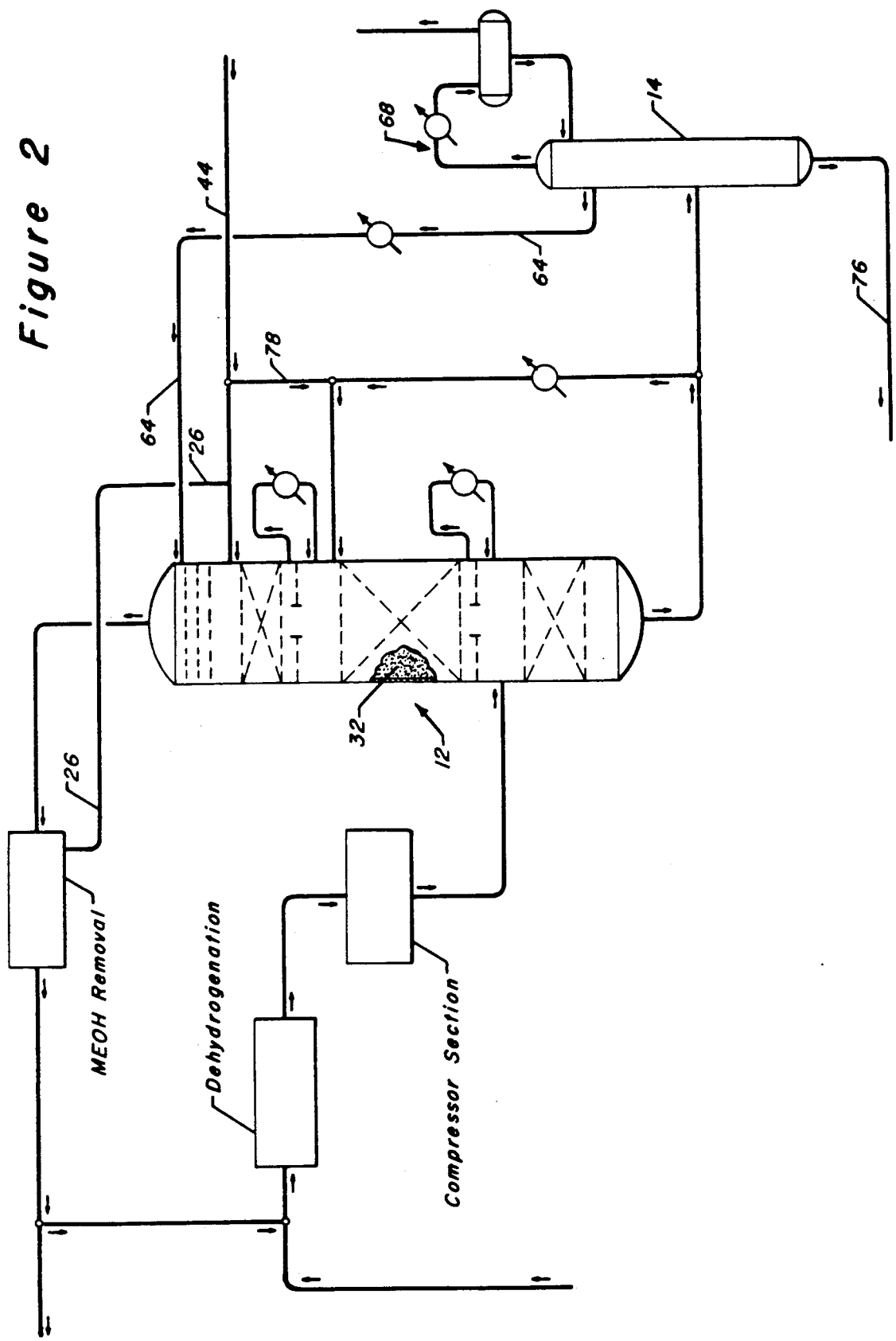

PROCESS FOR DIRECT ETHERIFICATION OF A DEHYDROGENATED EFFLUENT

BACKGROUND OF THE INVENTION

Field of the Invention

This invention relates broadly to the production of olefins. More specifically, this invention relates to the dehydrogenation of paraffinic hydrocarbons and the production of ether from the dehydrogenated paraffins.

INFORMATION DISCLOSURE

The combination of a dehydrogenation and etherification process is well known in the production of methyl tertiary butyl ether (MTBE) as a motor fuel additive. The production of MTBE uses $C_4$ isoolefins as a feedstock. A detailed description of processes including catalyst processing conditions and product recovery for the production of MTBE from isobutene and methanol are provided in U.S. Pat. Nos. 2,720,547 and 4,219,678 and in an article beginning at page 35 of the Jun. 25, 1979 edition of Chemical and Engineering News. The preferred process is described in a paper presented at the American Institute of Chemical Engineers, 85th National Meeting on Jun. 4-8, 1978 by F. Obenaus et al. The $C_4$ isoolefin feed to the MTBE process is typically obtained by the dehydrogenation of isobutane. Processes for dehydrogenating light paraffins are well known. One such process that converts LPG to monoolefins is discussed beginning at page 96 of the Dec. 8, 1980 edition of the Oil and Gas Journal and in an article beginning at page 191 of the Nov. 10, 1980 edition of the Oil and Gas Journal. A number of flow schemes have been proposed where a portion of the dehydrogenation zone effluent passes to an etherification zone. Combinations such as these are shown in U.S. Pat. Nos. 4,118,425 and 4,465,870. More complete representations of a flow arrangement for passing the dehydrogenation zone effluent to an etherification zone are shown in U.S. Pat. Nos. 4,329,516 and at page 91 of the October 1980 edition of Hydrocarbon Processing. The latter two references depict the typical gas compression and separation steps that are used to remove hydrogen and light ends from the dehydrogenation zone effluent before it passes to the etherification zone.

The etherification zone will typically produce unreacted alcohol and unreacted hydrocarbons including light hydrocarbon gases. The presence of unreacted alcohol and unreacted hydrocarbons in the effluent from the etherification zone results from equilibrium limitations on the reaction that takes place therein. In order to obtain a more complete reaction of the feed components, the use of catalytic distillation type reactors have been utilized for the etherification. U.S. Pat. No. 4,307,254 discloses a catalytic distillation process for the production of MTBE where a mixed feed of normal and isoolefins and a methanol stream are introduced into the lower and upper ends of a fixed bed of cationic exchange resin. The feed components are concurrently fractionated as the reaction proceeds so that MTBE is withdrawn from the bottom of the column and an unreacted hydrocarbons are withdrawn above the resin bed. U.S. Pat. No. 4,504,687 discloses another etherification process that uses a catalytic distillation type reactor that include a second distillation zone above a fixed bed of catalyst with the second distillation zone serving to remove alcohol and trace amounts of ether from the overhead vapor.

BRIEF SUMMARY OF THE INVENTION

This invention is a combination dehydrogenation and etherification process for the production of MTBE that discharges the effluent from the dehydrogenation zone to an etherification zone without separation and obtains a recycle hydrocarbon stream for the dehydrogenation zone as an overhead from the etherification zone. The dehydrogenation zone will process a feed stream made up primarily of normal and branched butanes, but also containing lesser quantities of light gases. The dehydrogenation zone produces an equilibrium mixture of isobutane and isobutene as well as other $C_4$ hydrocarbons and small quantities of lighter gases. The effluent from the dehydrogenation zone is increased in pressure to a level that will allow passage of the effluent through the fixed catalyst beds of the etherification zone and the recycle of isobutane and hydrogen as well as other trace components to the dehydrogenation zone. Isobutane, hydrogen, and other light components are removed as a vapor phase from the top of the MTBE reactor. A liquid phase stream containing MTBE is withdrawn from the bottom of the etherification zone along with unreacted methanol, and small amounts of dissolved isobutane and lighter hydrocarbons. The bottoms stream enters a deisobutanizer column for recovery of isobutane and methanol which is recycled to the etherification zone. The deisobutanizer column may also remove $C_3$ and lighter hydrocarbons as an overhead. Where the amount of methanol in the etherification zone bottoms stream is low, MTBE product may be recovered directly from the bottom of the deisobutanizer column. If a large excess of methanol is present, the MTBE product is carried over along with an MTBE and methanol azeotrope to an azeotrope column from which MTBE is recovered as a bottoms stream. Methanol MTBE azeotrope mixture recovered as an overhead from the azeotrope column can be recycled to the reaction zone.

In contradistinction to the prior art, this invention takes the entire efflent from the dehydrogenation zone and processes it in a catalytic reactor for the conversion of isobutane and methanol into MTBE. By the method of this invention, no separation facilities are required between the dehydrogenation zone and the etherification reactor. In addition, the etherification reactor converts the isobutene produced in the dehydrogenation zone into MTBE and thereby removes them from the isobutane recycle stream which is recovered as an overhead from the etherification zone. The direct transfer of the dehydrogenation zone effluent to the etherification zone and the reacting out of monoolefins facilitates recycle of the hydrogen and isobutane to the dehydrogenation zone and promotes energy savings in the process. These energy savings stem from the elimination of costly separation facilities for the removal of $C_3$ and lighter hydrocarbons ahead of the etherification zone and the substitution of such facilities downstream of the etherification zone which due to the conversion and removal of isobutene in the etherification zone leave a smaller quantity of hydrocarbons to be processed for the removal of the $C_3$ and lighter hydrocarbons.

Accordingly in one embodiment, this invention is a process for producing MTBE which starts by charging a feed stream containing isobutane and at least a portion of a first recycle stream containing isobutane and hydrogen to a dehydrogenation zone and recovering a first effluent containing isobutene, other $C_4$ hydrocarbons, and lighter hydrocarbons and hydrogen. The effluent is maintained at a pressure in a range of from 350-1400 kPag. The effluent passes without separation to an etherification zone at least partially vapor phase inlet conditions. A separately charged stream of methanol also enters the etherification zone. Isobutene from the first effluent contacts the methanol, and an etherification catalyst in the etherification zone. A liquid bottoms stream containing MTBE is withdrawn as a second effluent stream from the bottom of the reaction zone. The second effluent contains less than 5 wt. % isobutene and also contains methanol and dissolved $C_4$ and lighter hydrocarbons. $C_4$ and lighter boiling hydrocarbons are separated from the second effluent stream in a first separation zone and an MTBE effluent stream essentially free of $C_4$ hydrocarbons is recovered therefrom along with a second recycle stream comprising $C_4$ hydrocarbons and methanol. A third effluent stream containing isobutane and hydrogen is taken from the etherification zone. At least a portion of the second effluent stream is combined with the third effluent stream either directly or in the etherification zone. Methanol is removed from at least a portion of the third effluent stream to provide the first recycle which is essentially free of methanol.

BRIEF DESCRIPTION OF THE DRAWINGS

FIG. 2 is a modified version of the dehydrogenation/etherification process as shown in FIG. 1 wherein the azeotrope column 16 has been removed.

DETAILED DESCRIPTION OF THE INVENTION

Figure 1:
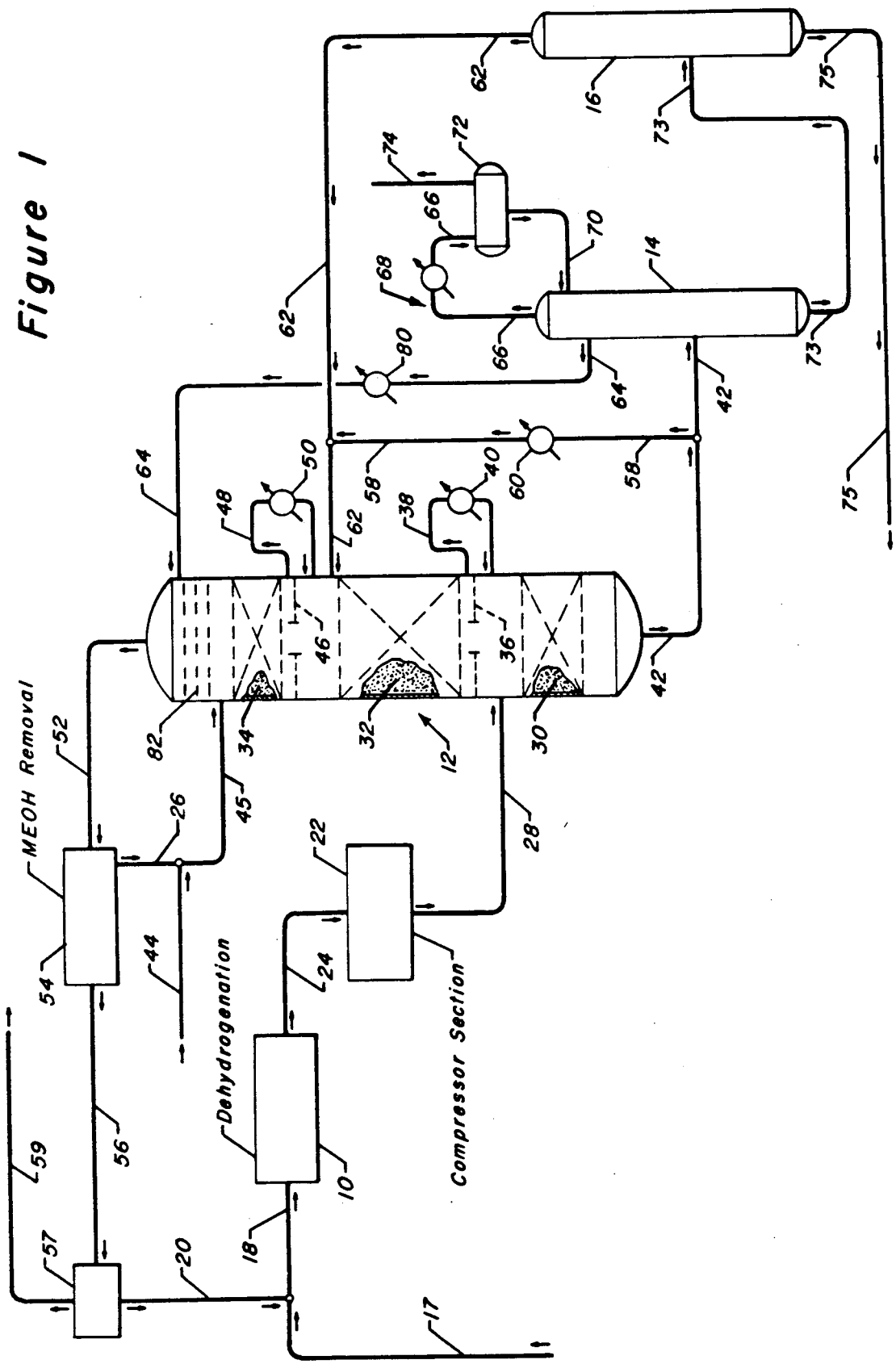
FIG. 1 shows a combined process for dehydrogenation and etherification having a dehydrogenation zone 10, an etherification zone 12 for receiving the effluent from the dehydrogenation zone, a $C_4$ distillation column 14 for separating the effluent from the etherification zone, and an azeotrope column 16 for recovering an MTBE product.

One component of this invention is a dehydrogenation zone for the production of olefins from dehydrogenation hydrocarbons. FIG. 1 shows the dehydrogenation zone represented schematically by box 10. Line 17 carries the primary feed to the dehydrogenation zone. Dehydrogenatable hydrocarbons for this invention are hydrocarbons having 4 carbon atoms per molecule and saturated carbon bonds which may be unsaturated by the dehydrogenation process. A substantial portion of the dehydrogenatable hydrocarbons will be isobutane and the dehydrogenation process will produce isobutene. Suitable feed for the dehydrogenation zone will often contain light hydrocarbons (i.e., those having less than four carbon atoms) which, for the purpose of this invention, serve as contaminants.

Along with the dehydrogenatable hydrocarbons, the feed to the dehydrogenation zone of the present invention comprises an $H_2$ rich stream, preferably containing at least 75 mole percent $H_2$. The presence of $H_2$ within the dehydrogenation zone serves several purposes. First, the $H_2$ acts to suppress the formation of hydrocarbonaceous deposits on the surface of the catalyst, more typically known as coke. Secondly, $H_2$ can act to suppress undesirable thermal cracking. Because $H_2$ is generated in the dehydrogenation reaction and comprises a portion of the effluent, the $H_2$ rich stream introduced into the reaction zone generally comprises recycle $H_2$ derived from separation of the dehydrogenation zone effluent. Alternately, the $H_2$ may be supplied from suitable sources other than the dehydrogenation zone effluent. In FIG. 1, line 20 transfer $H_2$ and recycle dehydrogenatable hydrocarbons from a hereinafter described source to line 18.

The combined dehydrogenatable hydrocarbon and $H_2$ are introduced into dehydrogenation reaction zone 10 via line 18. The dehydrogenation reaction zone of this invention preferably comprises at least one radial flow reactor through which the catalytic composite gravitates downwardly to allow a substantially continuous replacement of the catalyst with fresh and/or regenerated catalyst. A detailed description of the moving bed reactors herein contemplated may be obtained by reference to U.S. Pat. No. 3,978,150 which relates to a reactor system for the dehydrogenation of paraffinic hydrocarbons and U.S. Pat. No. 3,647,680 which illustrates a continuous catalyst regeneration system for use therewith. The dehydrogenation reaction is a highly endothermic reaction which is typically effected at low (near atmospheric) pressure conditions. The precise dehydrogenation temperature and pressure employed in the dehydrogenation reaction zone will depend on a variety of factors such as the composition of the paraffinic hydrocarbon feedstock, the activity of the selected catalyst, and the hydrocarbon conversion rate. In general, dehydrogenation conditions include a pressure of from about 0 to about 3500 kPag and a temperature of from about 480° C. to about 760° C. A suitable hydrocarbon feedstock is charged to the reaction zone and contacted with the catalyst contained therein at a liquid hourly space velocity of from about 1 to about 10. Hydrogen, principally recycle hydrogen, is suitably admixed with the hydrocarbon feedstock in a mole ratio of from about 0.1 to about 10. Preferred dehydrogenation conditions, particularly with respect to $C_3$-$C_5$ paraffinic hydrocarbon feedstocks, include a pressure of from about 0 to about 2000 kPag and a temperature of from about 540° C. to about 705° C., a liquid hourly space velocity of from about 1 to about 5, and a hydrogen/hydrocarbon mole ratio of from about 0.5 to about 2.

The dehydrogenation zone of this invention may use any suitable dehydrogenation catalyst. Generally, the preferred catalyst comprises a platinum group component, an alkali metal component, and a porous inorganic carrier material. The catalyst may also contain promoter metals which advantageously improve the performance of the catalyst. It is preferable that the porous carrier material of the dehydrogenation catalyst be an absorptive high surface area support having a surface area of about 25 to about 500 m²/g. The porous carrier material should be relatively refractory to the conditions utilized in the reaction zone and may be chosen from those carrier materials which have traditionally been utilized in dual function hydrocarbon conversion catalyst. A porous carrier material may, therefore, be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxides such as alumina, titanium dioxide, zirconium dioxides, magnesia, silica alumina, alumina boria, etc.; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/10 inch.

The preferred dehydrogenation catalyst also contains a plantinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or an elemental metal or in combination with one or more other ingredients of the catalyst. It is believed that the best results are obtained when substantially all the platinum group components exist in the elemental state. The platinum group component generally comprises from about 0.01 to about 2 wt. % of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali metal may range from about 0.1 to 5 wt. %, but is preferably between 1 and about 4 wt. % calculated on an elemental basis. This component may be added to the catalyst by the methods described above as a separate step or simultaneously with the solution of another component. With some alkali metals, it may be necessary to limit the halogen content to less than 0.5 wt. % and preferably less than 0.1 wt. %, while others may have higher halogen content.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

Referring then to FIG. 1, a hydrocarbon input stream comprising isobutane is charged to line 17. The feed stream is combined with the contents of line 20 which comprises a hereinafter described recycle stream containing hydrogen and mixed $C_4$ hydrocarbons to obtain a dehydrogenation feed stream which passes to dehydrogenation zone 10 via line 18. In zone 10, the dehydrogenation feed stream is heat exchanged, heated, and transported to a dehydrogenation reactor section at a temperature of about 500°–700° C. and at a pressure of about 300–500 kPag.

Preferably, dehydrogenation zone 10 includes multiple stacked or side by side reaction zones, and a combined stream of hydrogen and hydrocarbon feed is processed in series flow through said zones each of which contains a particulate catalyst disposed as an annular-form bed movable downwardly through said zones. The combined stream is then processed through said annular-form beds in a substantially radial flow and, since the dehydrogenation reaction is endothermic in nature, intermediate heating of the reactant stream between zones is the preferred practice.

Regardless of the actual reactor details, the hot effluent stream from the reaction zones is heat exchanged against the incoming feed for heat recovery purposes. After heat exchange, effluent from dehydrogenation zone 10 which consists of mixed $C_4$'s having a high concentration of isobutene, light hydrocarbons, and hydrogen at a temperature of about 50°–150° C. and a pressure slightly above atmospheric is carried to a compressor section 22 via line 24. Heat exchange of the effluent against the incoming feed reduces the effluent temperature to a point where passage through a compressor section will put the effluent at the desired inlet temperature for the MTBE unit. The compressor section raises the pressure of the dehydrogenation zone effluent from slightly above atmospheric to 300–700 kPag. This pressure is substantially lower than that usually required when a separation of light hydrocarbons and hydrogen is performed on the effluent from the dehydrogenation zone. In the arrangement of this invention, the discharge pressure from the compressor section need only reach that necessary to recycle unreacted component from the etherification reactor 12 back to the dehydrogenation process as further described herein. The dehydrogenation zone effluent enters the etherification reactor 12 at the discharge point of a line 28 and at a temperature of 40°–80° C. At these conditions, the dehydrogenation zone effluent is in vapor phase when it enters the etherification zone.

The etherification zone will contain one or more beds of an acidic catalyst that is maintained at etherification conditions. A wide range of materials are known to be effective as etherification catalysts for the reaction of isobutene and linear alkyl alcohols. These catalysts include mineral acids such as sulfuric acid, boron trifluoride phosphoric acid on kieselguhr, phosphorous-modified zeolites, heterol poly acids, and various sulfonated resins. The use of a sulfonated solid resin catalyst is preferred. These resin-type catalysts include the reaction products of phenolformaldehyde resins and sulfuric acid and sulfonated polystyrene resins including those crosslinked with divinylbenzene. Further information on suitable etherification catalysts may be obtained by reference to U.S. Pat. Nos. 2,480,940, 2,922,822, and 4,270,929. Suitable etherification conditions include superatmospheric pressure generally below 2000 kPag and a temperature between about 30° C. and about 100° C. A preferred temperature range for the process is from 50°-100° C. The actual operating conditions in the etherification zone are selected such that a substantial amount of the effluent from the compression section will be in vapor phase as it enters. It is preferred that the operating conditions for the etherification zone be selected such that the entire effluent from the compressor section is in vapor phase as it enters. Optionally, for the purposes of obtaining complete vaporization of the effluent, it will be brought to conditions of about 350 kPag and 60° C. when it enters the etherification zone.

Methanol feed may be added to the top of the etherification catalyst bed or when there is more than one bed it may also be added at intermediate points between catalyst beds. The catalyst beds may be cooled to remove exothermic heat of etherification reaction and prevent excessive temperatures in the catalyst bed which lead to vaporization and transport of MTBE products through the bed. In the process of FIG. 1, a portion of the methanol reactant is added to the top of a bed 32 and descends countercurrently to the rising hydrogen and $C_4$ vapors. The methanol entering above bed 32 may consist of a fresh methanol stream or methanol recycled with MTBE product or a combination of the two. In the preferred embodiment of this invention, a portion of the product stream containing methanol and MTBE is recycled to the top of bed 32. A substantial portion of the methanol entering above bed 32 will be in liquid phase. In simplest form, the etherification zone will contain one catalyst bed as previously described. FIG. 1 shows a preferred arrangement for the etherification zone wherein the etherification catalyst is separated into three distinct beds comprising a lower bed 30, an intermediate bed 32, and an upper bed 34. Effluent from the compressor section enters the etherification reactor 12 between lower and intermediate beds 30 and 32. Vapors from line 28 rise into contact with the catalyst in bed 32 wherein isobutene reacts with methanol to form MTBE which drops from bed 32 and continues downward through bed 30. An inter cooler tray 36 receives a portion of the MTBE product and downward flowing reactants from bed 32. Products and reactants are withdrawn by line 38 and passed through inter cooler 40 to remove heat produced by the exothermic reaction. Line 38 returns cooled product and reactants to the reaction zone to maintain a temperature of between 50°-80° C. between beds 32 and 30. The multiple catalyst bed arrangement promotes the complete reaction of isobutene in the reaction zone so that further separation of isobutene from the other $C_4$ hydrocarbons will not be necessary for the bottoms effluent from the reaction zone. Lower catalyst bed 30 receives any unreacted isobutene that drops from catalyst bed 32 or is carried downward by the descending fluid from catalyst bed 32. Any isobutene that enters bed 30 reacts with methanol that is also present in the descending fluid, so that the product stream has an isobutene concentration that is at least below 5 mol. %. The product stream is recovered from the bottom of reaction zone 12 through line 42 for further recovery and/or recycle. $C_4$ vapors which may still contain trace amounts of isobutene rise from bed 32 into upper bed 34 where they are contacted countercurrently with a methanol-containing stream that enters the reaction zone at the top of bed 34 through line 45. The methanol stream again may be either fresh methanol added to the process or a recycle stream containing methanol. Regardless of its source, methanol added to the top of reactor 34 is in liquid phase. Inter cooler tray 46 positioned below upper bed 34 collects a portion of the descending fluid which is taken by line 48 and passed through inter cooler 50 in order to maintain temperatures in bed 34 within a desired etherification range. Rising $C_4$ and lighter hydrocarbons are collected overhead and returned by line 52 to hydrogenation zone 10.

The etherification zone yields an overhead that has very little isobutene. Operation and arrangement of the etherification to consume essentially all of the isobutene in the production of MTBE keeps the concentration of isobutene in the overhead at very low levels.

The overhead from line 52 provides the recycle of hydrogen and $C_4$ hydrocarbons to the dehydrogenation zone. A significant quantity of methanol on the order of 1-5 wt. % of the total stream may be carried over with the overhead stream. Therefore, the stream is first passed through a methanol removal zone 54. The particular method of methanol removal is not an important aspect of this invention. Water wash and absorbent methods have proved satisfactory for methanol removal and either one may be employed. Such methods are well known to those skilled in the art. Recovered methanol is returned to reaction zone 12. Methanol from removal zone 54 may be added to the etherification zone at any convenient point and for the purposes of the preferred embodiment is shown being taken by line 26, combined with fresh methanol feed from line 44 and taken by line 45 for return to the etherification zone at a point above bed 34. The methanol-free effluent from zone 54 is taken by line 56 where at least a portion of the stream is returned by line 20 to the dehydrogenation zone 10 as the hereinbefore mentioned recycle. The remainder of the mixed $C_4$'s hydrogen and any light hydrocarbons are recovered by line 56 as a net gas which may be further separated for additional uses. FIG. 1 shows the preferred mode where this stream enters a separation zone 57 that separates at least a portion of the hydrogen and light hydrocarbons from $C_4$ hydrocarbons. The separated hydrogen and light hydrocarbons are removed from the process by line 59 while the remaining $C_4$ hydrocarbons, hydrogen, and light ends return to the process via line 20.

The ratio of total methanol entering the etherification zone is maintained in a ratio of alcohol to isobutane in a broad range of 1:1 to 2:1. An excess of methanol above that required to achieve satisfactory conversion at good selectivity should be avoided as some decomposition of methanol to dimethyl ether may occur.

As the isobutene containing stream rises through the catalyst bed, a majority of the isobutene is reacted with the methanol to form MTBE product. Due to the exothermic nature of the reaction intercoolers may be provided between multiple catalyst beds to keep the reactants at the desired temperature. Once formed the relatively heavier MTBE product drops from the catalyst bed and eventually to the bottom of the etherification zone where it is collected and transferred to a further separation zone. The MTBE reaction zone is maintained at conditions that will keep the methanol and MTBE product in liquid phase. The MTBE product that is collected from the bottom of the etherification zone also contains unreacted methanol and mixed $C_4$ hydrocarbons which are dissolved in the stream and deficient in isobutene. Additional light gases that enter with the effluent from the compressor section may be absorbed in the downward moving stream of products and reactants as it passes through reaction zone 12 and recovered with the MTBE product stream.

A portion of the MTBE product stream may be recycled to the top of the etherification catalyst bed either directly or after further separation. Recycling of the product stream or product stream fraction provides the necessary liquid traffic for the vapor liquid content of the reaction zone and serves to maximize the etherification yield. Such further separation may also include the recovery of a $C_4$ methanol azeotrope which is returned to the top of the etherification catalyst bed.

The effluent from the bottom of reaction zone 12 enters further separation facilities for the recovery of the MTBE product, unreacted methanol, and recycle $C_4$'s. In the preferred embodiment of this invention, a portion of the bottoms stream carried by line 42 is diverted through a line 58. The diverted portion of the bottoms stream passes through a heat exchanger 60 that cools the diverted materials which are then returned to the top of intermediate bed 32. The diverted materials may be first joined with a hereinafter described recycle stream of MTBE and methanol in a line 62. In this manner, the temperature of the diverted materials may be adjusted such that the combined stream entering reaction zone 12 through line 62 will have a temperature in the range of from 40°–70° C. A relatively large circulation of MTBE and methanol through line 58 is preferable in order to maintain more than stoichiometric methanol at the bottom of bed 32 and provide better vapor-liquid contact on surface of the etherification catalyst.

That portion of the bottoms stream from reactor 12 that is not diverted as reflux enters a separation zone for the recovery of the MTBE product. This separation zone may consist of one or more columns. FIG. 1 shows the effluent from reactor 12 entering $C_4$ distillation column 14 for the removal of $C_4$ and lighter hydrocarbons. Column 14 is a multi-tray fractionation column. $C_4$'s and lighter hydrocarbons rise to the top of the column. $C_4$'s are removed from the column via line 64 which is taken as a sidecut from an upper portion of the column. The mixed $C_4$'s taken by line 64 are ultimately returned, at least in part, as recycle to the dehydrogenation zone 10. Some methanol may also be entrained with the $C_4$ sidecut which is returned to reaction zone 12. An overhead stream consisting principally of $C_3$ and lighter hydrocarbons that were absorbed with the MTBE product stream is taken overhead via line 66 into a condenser section 68. Condenser section 68 returns reflux of $C_3$ and any heavier hydrocarbons to column 14 through a line 70. Overhead vapors consisting of non-condensible $C_3$ and lighter hydrocarbons are recovered from a separator drum 72 by line 74. Where the quantities of $C_3$ and lighter hydrocarbons from the dehydrogenation are small, almost all of these materials will be recovered in the overhead from the condenser section. Depending upon its composition, the $C_3$ stream from line 74 may be used as fuel gas or further separated for additional product recovery. A mixture of MTBE and methanol is recovered from the bottom of a $C_4$ removal column 14 by line 73. In most cases, the concentration of methanol mixed with the product in line 73 will be high enough that MTBE and methanol will be transferred to an azeotrope column 16 for separation of methanol from the MTBE. Column 16 separates the methanol and MTBE mixture into a methanol MTBE azeotrope that is recovered overhead by line 62 and a relatively methanolfree MTBE product that is recovered from the bottom of column 16 by line 75. In the preferred embodiment depicted by FIG. 1, the MTBE methanol azeotrope is combined with the diverted portion of the effluent from reactor 12, as previously described, and introduced into reactor 12 above intermediate bed 32.

The mixed $C_4$ and methanol sidecut stream taken by line 64 can be recycled directly to a methanol removal zone for the recycle of mixed $C_4$ to dehydrogenation zone or, as shown in FIG. 1, added to the top of reactor 12 for a further separation of methanol from the recycle $C_4$ hydrocarbons. As shown by the process in FIG. 1, the mixed $C_4$'s and methanol stream carried by line 64 passes through a heat exchanger 80 where it is cooled and then enters reactor 12 above upper bed 34 at the top of a series of fractionating trays 82. Trays 82 effect a further separation of methanol from the mixed $C_4$'s as additional $C_4$'s rise in countercurrent contact with the mixture of methanol and $C_4$. In this manner, a substantial portion of the methanol that would otherwise be recovered by methanol removal zone 54 is separated in the top of reactor 12. The relatively large quantity of hydrogen that enters the etherification zone with the dehydrogenation zone is primarily recovered overhead with the $C_4$'s.

In those cases where the methanol to isobutene ratio can be maintained at stoichiometric levels or at about 1.05 such that excess methanol and the MTBE product from reactor 12 can be kept at a minimum, an alternate flow scheme as shown in FIG. 2 may be employed. In the flow scheme of FIG. 2, the effluent from reactor 12 is transferred to a $C_4$ column in substantially the same manner as previously described. Column 14 again recovers $C_3$ and lighter hydrocarbons from an overhead condenser section 68 and returns a $C_3$ reflux plus any heavier hydrocarbons to the top of the column 14. $C_4$ hydrocarbons are recovered as a sidecut by line 64. Excess methanol that enters column 14 with the product stream from reactor 12 is also removed from the distillation column with the sidecut taken by line 64. The low concentration of methanol entering the distillation column and its nearly complete removal by a sidecut 64, allows the MTBE product to be recovered from the bottom of column 14 with a very low methanol concentration. The MTBE product recovered from the bottom of the column can be used directly as a high octane blending component. MTBE product is recovered by line 76. With the elimination of the azeotrope column, the MTBE methanol stream that was recovered therefrom is no longer available for recycle to reactor 12 above bed 32. In order to provide the necessary methanol addition at the top of bed 32, a portion of the fresh methanol which enters the reactor through line 44 and recycle methanol which enters the process through line 26 is diverted through a line 78 and mixed with the recycled MTBE product stream from the bottom of reactor 12.

This invention will be further described in the context of an example for the production of MTBE. The description of this invention in the terms of this specific process example is not meant to limit this invention to the particular details disclosed therein. This example is based on engineering calculations and experience with the operation of similar process units. This example makes reference to the process configuration shown in FIG. 1 which is only a schematic drawing for this type of operation. FIG. 1 shows only those compressors, heat exchangers, coolers, and separators that are useful in the description of the process. The utilization of other miscellaneous hardware such as heaters, valves, reboilers, pumps, instrumentation, and controls have been omitted as not essential to a clear understanding of the process. The use of such hardware being well within the purview of one skilled in the art. The attached Table lists the composition of materials in major process lines for the process, as practiced in the configuration of FIG. 1.

Starting then with the dehydrogenation zone 10 a feed mixture of $C_4$ hydrocarbons enters the process by line 17 and has the composition given in the Table. The feed mixture is combined with a recycle stream to provide a dehydrogenation zone input stream having the composition given in the following Table under line 18. In zone 10 the dehydrogenation feed stream is heat exchanged and transported to a dehydrogenation reactor section at a temperature of about 500°–700° C. and at pressure about 300–500 kPag. The dehydrogenation zone includes multiple stacked reactors in which the feed is contacted with a dehydrogenation catalyst comprising platinum on an alumina carrier. Line 24 recovers the effluent stream from the dehydrogenation zone after heat exchange at a temperature of 50°–150° C. and a pressure of slightly above atmospheric. The composition of the effluent is given in the Table.

The contents of line 26 enter an etherification zone 12 having the three bed arrangement as previously described. The catalyst beds and other internals of the etherification zone vary the pressure as well as the temperature throughout reaction zone 12. Vapor-liquid contacting trays 82 operate at about a pressure of 300–500 kPag and a temperature of 30°–80° C. Catalyst bed 34 has an average temperature of 60°–70°C. The lower portion of bed 32 has a temperature of about 65°–80° C. The purpose of bed 30 is to prevent carry over of isobutene in the bottoms stream from the reactor section, therefore, the reaction releases little heat into the lower bed which has a temperature of about 70°–80° C. A bottoms stream is withdrawn by line 42 at a temperature of 60°–80° C. and a pressure of 300–500 kPag. At least 50% of the contents of line 42 is taken by line 58, cooled to approximately 40°–50° C., and returned to reaction zone 12 via line 62. The remainder of the contents from line 42 enter column 14. In the upper portion of column 14, a sidecut stream containing mixed $C_4$'s and methanol is taken by line 64. The contents of line 64 are recycled to the vapor-liquid contacting trays 82 of reactor zone 12 after cooling to a temperature of 40°–50° C. in heat exchanger 80. Additional overhead materials comprising $C_4$'s and lighter hydrocarbons are taken overhead from column 14 into condenser section 68. Light hydrocarbons dissolved in the MTBE reactor effluent are withdrawn via line 74 from separator drum 72 with the remainder of the overhead being returned as reflux to the top of the column. A methanol MTBE bottoms stream is taken by line 73 from the bottom of column 14 and injected into azeotrope column 16 at approximately its midpoint. Column 16 performs a further separation of methanol and MTBE such that a relatively pure MTBE product containing less than 100 ppm methanol is recovered from the bottom of the column via line 75. The Table shows the compositions of the contents of line 75. An overhead stream, at least a portion of which includes MTBE and methanol as an azeotrope, is recovered from the top of column 16 by line 62 and recycled to MTBE reaction zone.

| | Compositions in mol % | | | | |
|---|---|---|---|---|---|
| | Line 17 | Line 18 | Line 24 | Line 44 | Line 75 |
| $H_2$ | | 44.2 | 52.6 | | |
| $C_1$ | | 6.7 | 8.3 | | |
| $C_2$ | | 0.2 | 0.6 | | |
| $C_3$ | 1 | 1/7 | 2.5 | | |
| isobutane | 98 | 46.3 | 18.6 | | TR |
| isobutene | | TR | 16.6 | | TR |
| Other $C_4$'s | 1 | 0.9 | 0.8 | | 0.4 |
| $C_5$ & heavier hydrocarbons | TR | | | | |
| MEOH | — | — | — | 99.9 | 0.1 |
| TBA | — | — | — | — | 0.1 |
| MTBE | — | — | — | — | 99.4 |
| $H_2O$ | — | — | — | 0.1 | — |
| | 100 | 100 | 100 | 100 | 100 |

As can be seen from the Table and the foregoing text, methanol is recycled to the reaction zone via lines 26, 58, and 62. Fresh methanol is added by line 44 at a location above that 34. The methanol addition rate through line 44 is maintained such that the total input of methanol from recycle and line 44 will maintain a mole ratio of methanol to isobutene feed in the range of 1:1 to 1.1:1.

The Example demonstrates that a high quality MTBE product is obtained by the method of this invention. Charging the dehydrogenation zone effluent without prior separation to the etherification zone 12 greatly simplifies to flow scheme and allows the process to be carried out more economically without any detriment to the product obtained thereby. Furthermore, the separation facilities that are used can be reduced in size due to the lower volume of material that enters the recycle recovery facilities downstream of the etherification zone and the recovery of recycled material in the etherification zone.

What is claimed is:

1. A process for producing MTBE comprising:
    (a) charging a feed stream comprising isobutane and at least a portion of a first recycle stream to a dehydrogenation zone, said recycle stream comprising isobutane and hydrogen, dehydrogenating said isobutane in said dehydrogenation zone, and recovering a first effluent stream comprising $C_4$ and lighter hydrocarbons, and hydrogen, said $C_4$ hydrocarbons of said first effluent stream including isobutene and isobutane;
    (b) passing said first effluent to an etherification zone without separation at inlet conditions that will maintain at least a portion of said $C_4$ hydrocarbons in vapor phase;
    (c) contacting isobutene from said first effluent stream with methanol in an etherification zone at etherification conditions and in the presence of an etherification catalyst;
    (d) recovering a second effluent stream from said etherification zone having less than 5 mol. % isobutene and comprising MTBE, methanol and $C_4$ and lighter boiling hydrocarbons and discharging isobutane and hydrogen from said etherification zone;

(e) separating C$_4$ and lighter boiling hydrocarbons from said second effluent stream in a first separation zone and recovering an MTBE effluent stream essentially free of C$_4$ hydrocarbons, and a second recycle stream comprising C$_4$ hydrocarbons and methanol;

(f) combining at least a portion of said second recycle stream with said isobutane and hydrogen of said etherification zone to generate a third recycle stream; and (g) charging said third recycle stream to a methanol removal zone and removing methanol from at least a portion of said third recycle stream to provide said first recycle stream.

2. The process of claim 1 wherein said first effluent stream enters said etherification zone at a temperature in the range of 50°-80° C. a pressure in the range of 300-500 kPag.

3. The process of claim 1 wherein methanol and isobutene are in countercurrent contact in said etherification zone.

4. The process of claim 1 wherein said etherification zone is arranged as a series of beds and said first effluent stream enters at a point intermediate two of said catalyst beds.

5. The process of claim 1 wherein at least a portion of said second effluent stream is recycled directly to said etherification zone.

6. The process of claim 1 wherein said second recycle stream is passed to the top of said etherification zone.

7. The process of claim 1 wherein said MTBE effluent stream is passed to a second separation zone, an MTBE product stream relatively free of methanol is recovered from said second separation zone, and a fourth recycle stream comprising a methanol and an MTBE azeotrope is recovered from said second separation zone and returned to said etherification zone.

8. The process of claim 1 wherein all of said first effluent stream enters said etherification zone in vapor phase.

9. A process for producing MTBE comprising:

(a) charging a feed stream comprising isobutane and at least a portion of a first recycle stream to a dehydrogenation zone, said recycle stream comprising isobutane and hydrogen, dehydrogenating said isobutane in said dehydrogenation zone, and recovering a first effluent stream comprising C$_4$ and lighter hydrocarbons and hydrogen said C$_4$ hydrocarbons of said first effluent stream including isobutene;

(b) maintaining an etherification zone at etherification conditions, said etherification zone having at least three vertically disposed beds of etherification catalyst therein;

(c) passing said first effluent without separation to said etherification zone at inlet conditions that maintain said first effluent in vapor phase and at a location between the uppermost and lowermost of said beds and countercurrently contacting at least a portion of said effluent with methanol in a bed located above the location where said first effluent passes into said etherification zone;

(d) recovering a second effluent stream from said etherification zone having less than 5 mol. % isobutene and comprising MTBE, methanol and C$_4$ and lighter boiling hydrocarbons;

(e) recycling at least a portion of said second effluent stream directly to said etherification zone as a second recycle stream;

(f) passing the remaining portion of said second effluent to a first separation zone and recovering a bottoms fraction comprising an MTBE effluent stream, relatively free of C$_4$ hydrocarbons, a middle cut comprising C$_4$ hydrocarbons and methanol, and an overhead fraction comprising C$_3$ hydrocarbons and higher boiling components;

(g) recycling said middle cut to said etherification zone at a location above said catalyst beds; and (h) recovering an overhead stream from said etherification zone comprising methanol, isobutane, other C$_4$ hydrocarbons, and hydrogen and passing said stream through a methanol removal zone to provide said first recycle stream.

10. The process of claim 9 wherein methanol added to said etherification zone does not exceed 10% of stoichiometric requirements.

11. The process of claim 9 wherein the recycled portion of said second effluent stream enters said etherification zone in a vapor phase.

12. The process of claim 9 wherein said middle cut is recycled to a series of separation trays said etherification zone.

13. The process of claim 9 wherein at least 25% of said second effluent stream is recycled directly to said etherification zone.

14. The process of claim 9 wherein fresh methanol is added to said etherification zone at a location above said catalyst beds.

15. The process of claim 9 wherein the catalyst in said etherification zone is arranged in three beds, and said first effluent enters said etherification zone between a lowermost and middle bed, said second effluent stream enters said etherification zone between said middle and an uppermost bed, and fresh methanol is added to said etherification zone at a location above said uppermost bed.

16. The process of claim 9 wherein said MTBE effluent stream is transferred to a second separation zone, an MTBE product is recovered from the bottom of said second separation zone and a third recycle stream comprising methanol and MTBE is recovered from the top of said second separation zone and recycled to said etherification zone.

17. The process of claim 16 wherein said etherification catalyst is divided into at least three beds, said second effluent stream enters said etherification zone between a lowermost and an intermediate bed, said second and third recycle streams enter said etherification zone between an intermediate and an uppermost bed, and fresh methanol is added to said etherification zone above said uppermost bed.

18. The process of claim 17 wherein a series of separation trays are located at the top of said etherification zone and said middle cut is cooled to a temperature in the range of 30°-60° C. and returned to said series of separation trays.

* * * * *